(12) United States Patent
Zhang et al.

(10) Patent No.: US 7,596,205 B2
(45) Date of Patent: Sep. 29, 2009

(54) X-RAY HYBRID DIAGNOSIS SYSTEM

(75) Inventors: Xiaoyan Zhang, Beijing (CN); Xuguang Sun, Beijing (CN); Xueli Wang, Beijing (CN); Zhe Shen, Beijing (CN)

(73) Assignee: GE Medical Systems Global Technology Company, LLC, Waukesha, WI (US)

( * ) Notice: Subject to any disclaimer, the term of this patent is extended or adjusted under 35 U.S.C. 154(b) by 0 days.

(21) Appl. No.: 11/777,656

(22) Filed: Jul. 13, 2007

(65) Prior Publication Data

US 2008/0013674 A1    Jan. 17, 2008

(30) Foreign Application Priority Data

Jul. 14, 2006    (CN) .......................... 2006 1 0110884

(51) Int. Cl.
*A61B 6/00*    (2006.01)
(52) U.S. Cl. ................. 378/9; 378/20; 378/92; 378/196; 378/209
(58) Field of Classification Search ............... 378/9–20, 378/101, 92, 98.2, 98.8, 116, 193–198, 208, 378/209
See application file for complete search history.

(56) References Cited

U.S. PATENT DOCUMENTS

| | | | |
|---|---|---|---|
| 5,327,474 A * | 7/1994 | Inoue et al. | 378/20 |
| 6,205,347 B1 | 3/2001 | Morgan et al. | 600/407 |
| 6,208,706 B1 * | 3/2001 | Campbell et al. | 378/9 |
| 6,661,866 B1 | 12/2003 | Limkeman et al. | 378/19 |
| 6,920,196 B2 | 7/2005 | Ueno et al. | 378/19 |
| 7,020,313 B2 | 3/2006 | Declerek et al. | 382/128 |

FOREIGN PATENT DOCUMENTS

JP    08280666 A2    10/2005

* cited by examiner

*Primary Examiner*—Courtney Thomas
(74) *Attorney, Agent, or Firm*—Armstrong Teasdale LLP

(57) ABSTRACT

An X-ray hybrid diagnosis system includes a single power supply, an X-ray radiography unit, an X-ray CT unit, and a single control console. The single power supply powers X-ray CR system having first X-ray tube and X-ray CT system having second X-ray tube. The X-ray radiography unit irradiates a subject with X-rays from first X-ray tube to obtain an X-ray radiographic image. The X-ray CT unit irradiates the subject with X-rays from the second X-ray tube and acquires projection data from a beam of the X-rays that has passed through the subject, to reconstruct an image using the acquired projection data, and to obtain a tomographic image. The single control console controls the X-ray radiography unit and the X-ray CT unit.

19 Claims, 15 Drawing Sheets

FIG.10
A
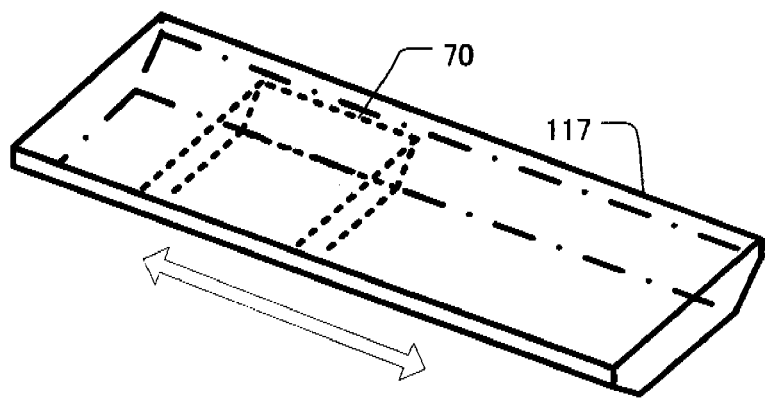
B
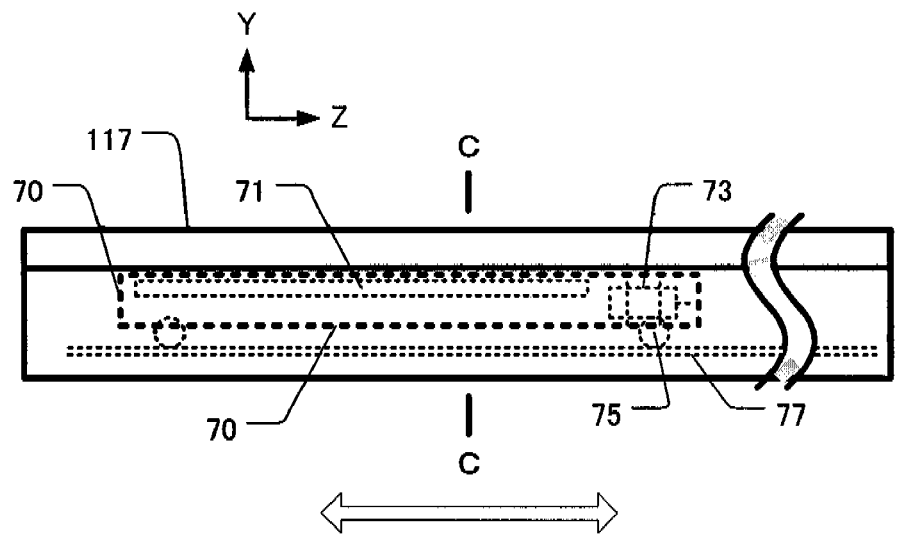
C
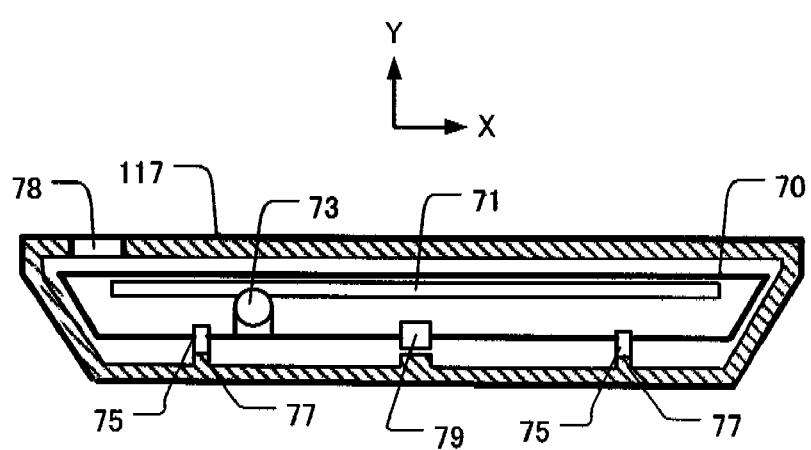

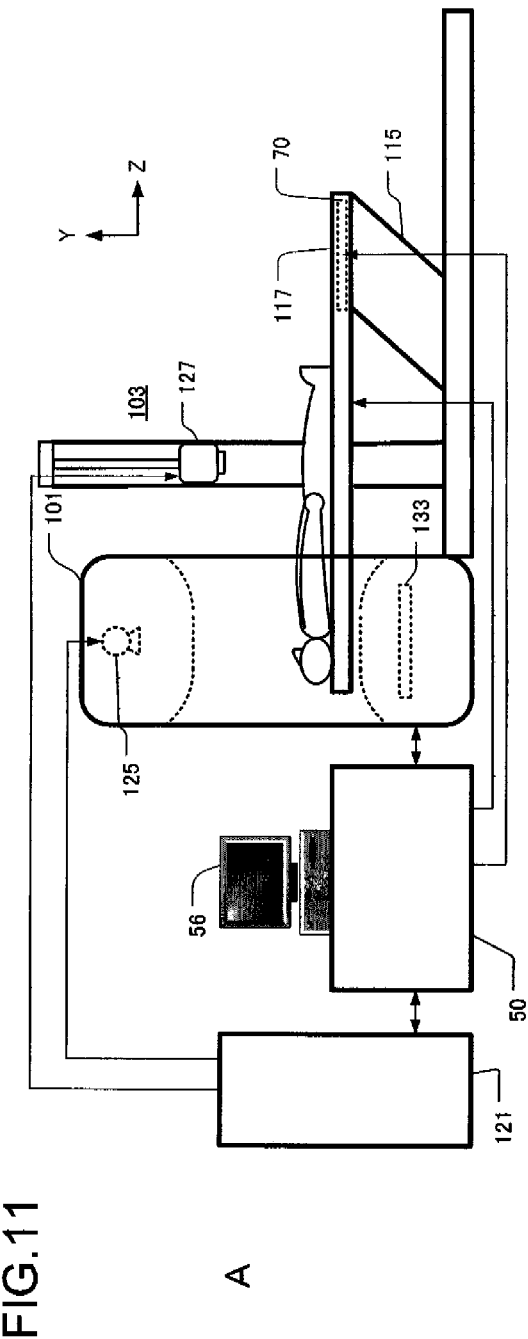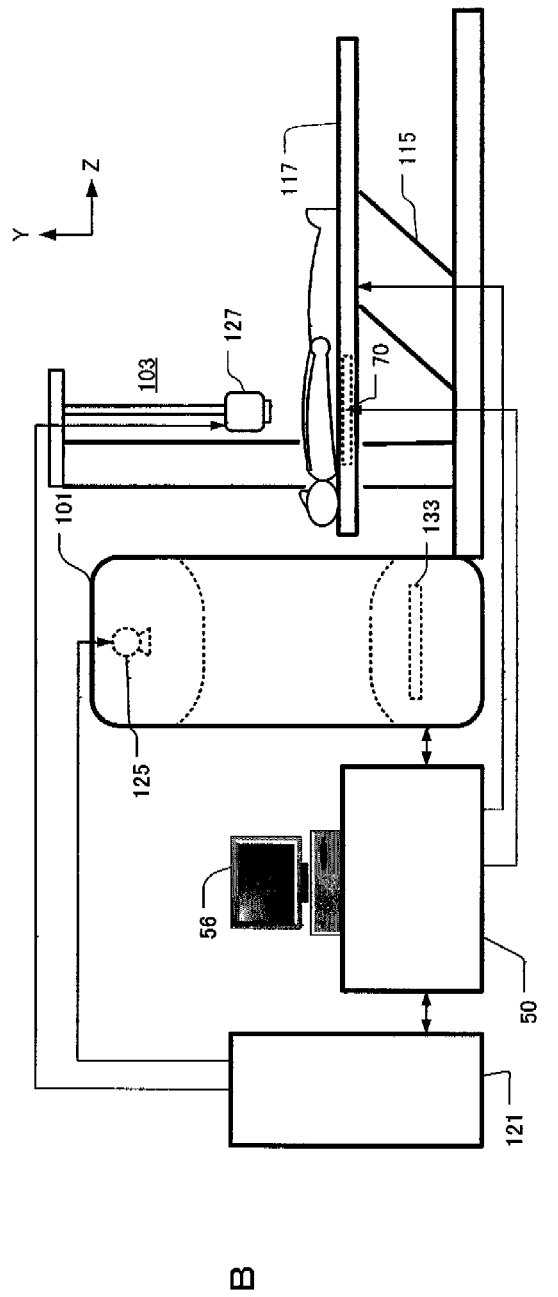
FIG.11

X-RAY HYBRID DIAGNOSIS SYSTEM

CROSS REFERENCE TO RELATED APPLICATIONS

This application claims the benefit of Chinese Application No. 200610110884.1 filed Jul. 14, 2006.

BACKGROUND OF THE INVENTION

This invention relates to an X-ray hybrid diagnosis system having an X-ray radiography system and a medical X-ray computed tomography (CT) system incorporated therein.

To make a diagnosis upon a patient, depending upon the conditions of the disease or injury of the patient, the X-ray computed radiography (CR) system is used to take radiographic or fluoroscopic images, or the X-ray CT system is used to acquire projection data for display of tomography images. Thus, hospitals should normally have the both systems equipped separately, which would disadvantageously involve considerable cost and take up a large footprint.

Moreover, a patient who has been subjected to the X-ray CR system to take radiographic images may subsequently have to be put through the X-ray CT system to have the tomography images inspected. In such instances, the patient should be moved from one room to the other room, which imposes extra strains on the patient. Related techniques hitherto proposed are disclosed for example in JP 8-280666 A.

SUMMARY OF THE INVENTION

For medium-sized or smaller hospitals in which not many patients receive treatment, it would be particularly desirable that diagnoses be efficiently given on patients at low cost, while reduction in maintenance cost would be in increasing demand. Therefore, it is an object of the present invention to provide an X-ray hybrid diagnosis system having an X-ray CR system and an X-ray CT system incorporated therein which may have a smaller footprint and serve to ease the strain on patients.

According to the present invention, the X-ray CR system and the X-ray CT system are not only placed in the same room but also combined or designed in a single hybrid system to avoid duplication by sharing as many members or devices as possible, so as to reduce the footprint. Such sharing of members or devices may contribute to reduction in manufacturing cost and maintenance cost. More specifically, the X-ray CR system and the X-ray CT system have a common power supply, so that measures to prevent overheating of each X-ray tube can be introduced to increase the longevity of the X-ray tubes, thus holding down the maintenance cost.

In a first aspect of the present invention, there is provided an X-ray hybrid diagnosis system comprising: a single power supply powering X-ray CR system having first X-ray tube and X-ray CT system having second X-ray tube; an X-ray radiography unit irradiating a subject with X-rays from the first X-ray tube to obtain an X-ray radiographic image; an X-ray CT unit irradiating the subject with X-rays from the second X-ray tube and acquiring projection data from a beam of the X-rays that has passed through the subject, to reconstruct an image using the acquired projection data, and to obtain a tomography image; a single control console controlling the X-ray radiography unit and the X-ray CT unit. The X-ray hybrid diagnosis system consistent with the first aspect of the present invention can make both of the X-ray radiography unit and the X-ray CT unit operable by the single power supply and the single control console, and can thus be implemented at a lower cost and in a smaller footprint than those which would otherwise be required when the power supply and the control console are provided for each X-ray tube and unit. From the viewpoint of patients, this system is designed to obviate the necessity of the patient moving from one room to the other room so as to take the radiographic image with the X-ray radiography unit and to get CT scanned with the X-ray CT unit, and thus can remove heavy strains which would otherwise be imposed on the patient.

In a second aspect, the X-ray hybrid diagnosis system consistent with the present invention further comprises a single cradle commonly usable for the subject to be irradiated with the X-rays from the first X-ray tube and irradiated with the X-rays from the second X-ray tube. The X-ray hybrid diagnosis system consistent with the second aspect of the present invention is designed to use the single cradle for both of the X-ray radiography unit and the X-ray CT unit, and can thus be implemented in a smaller footprint. Even if a patient lying in the cradle, who has been X-rayed (radiographed with X rays) to obtain radiographic images, is determined to be subsequently CT scanned, the patient need not be moved.

In a third aspect, the X-ray radiography unit consistent with the present invention comprises a first X-ray detector to obtain the X-ray radiographic image, and the first X-ray detector is located in the cradle. In the X-ray hybrid diagnosis system according to the third aspect of the present invention, the first X-ray detector is located in the cradle; therefore, an available workspace is kept unoccupied so that the X-ray hybrid diagnosis system can be operated with enhanced ease.

In a fourth aspect, the first X-ray detector consistent with the present invention is movable in the cradle. In the X-ray hybrid diagnosis system according to the fourth aspect of the present invention, the first X-ray detector is movable in the cradle; therefore, the first X-ray detector can be moved in accordance with a portion of the patient to be radiographed so that any portion required can be radiographed without moving the patient.

In a fifth aspect, the cradle provided in the X-ray radiography unit consistent with the present invention is bendable in structure. In the X-ray hybrid diagnosis system according to the fifth aspect of the present invention, the X-ray radiographic image can be obtained from the patient being in an unstrained or relaxed position.

In a sixth aspect, the cradle provided in the X-ray radiography unit consistent with the present invention is movable in a body-axial (rostrocaudal or longitudinal) direction of the subject and movable in a direction perpendicular to the body-axial direction of the subject. In the X-ray hybrid diagnosis system according to the sixth aspect of the present invention, the cradle can be adjusted in a vertical position; thus, the X-ray radiographic image can be obtained from the patient being in an unstrained or relaxed position.

In a seventh aspect, the control console consistent with the present invention comprises: a first mode in which the X-ray radiographic image is obtained by the X-ray radiography unit, and thereafter the projection data is acquired using the X-ray CT unit; and a second mode in which the projection data is acquired using the X-ray CT unit, and thereafter the X-ray radiographic image is obtained by the X-ray radiography unit; a third mode in which the X-ray radiographic image is obtained by the X-ray radiography unit; a fourth mode in which the projection data is acquired using the X-ray CT unit. In the X-ray hybrid diagnosis system according to the seventh aspect of the present invention, for example, the patient can be X-rayed to obtain radiographic images and thereafter CT scanned, without moving while lying (in a recumbent posture) in the cradle. Similarly, the patient can be CT scanned and thereafter X-rayed.

In an eighth aspect, the control console consistent with the present invention comprises means for predicting increase in temperature of each of the first and second X-ray tubes to keep a control on irradiation from the first and second X-ray tubes so that the temperature is held on or below a predetermined threshold. In other words, the control console is configured to exercise control over the irradiation from the first and second X-ray tubes so that the temperature as predicted of each of the first and second X-ray tubes would not increase beyond the predetermined threshold. In the X-ray hybrid diagnosis system according to the eighth aspect of the present invention, operation of the first and second X-ray tubes at the temperature above a permissible level is prohibited; thus, the possibility of breakdown can be reduced and the longevity of the X-ray tubes can be increased.

In a ninth aspect, the control console consistent with the present invention comprises means for offering an option of change in irradiation conditions of the first and second X-ray tubes, if the control console predicts increase in the temperature beyond the predetermined threshold. In the X-ray hybrid diagnosis system according to the ninth aspect of the present invention, the option of change in irradiation conditions is offered to the operator, in order that the operator is certain of obtaining images under the conditions such that the first and second X-ray tubes would never be caused to operate at temperatures beyond the permissible level. Therefore, the operator will be able to continue the image acquisition operation as far as the operator can carry out the operation under the irradiation conditions offered by the control console.

By making use of the X-ray hybrid diagnosis system consistent with the present invention, the power supply, the control console and such other components may be shared, to thereby render the footprint smaller. Moreover, sharing of its members and devices may contribute to reduction in the manufacturing cost and the maintenance cost.

BRIEF DESCRIPTION OF THE DRAWINGS

The above aspects, other advantages and further features of the present invention will become readily apparent from the following description of illustrative, non-limiting embodiments with reference to accompanying drawings, in which:

FIG. 8A is a front elevation for showing an operation of obtaining a chest image of the subject, FIG. 8B is a side elevation of FIG. 8A, FIG. 8C is a front elevation for showing an operation of obtaining an upper-arm image of the subject, and FIG. 8D is a side elevation of FIG. 8C;

FIGS. 10A-10C show a structure of a third cradle 117 in which a flat panel detector 70 is incorporated inside;

FIG. 11A illustrates an operation of the gantry 101 as the CT unit obtaining X-ray tomographic images of a subject in a decubitus position, and FIG. 11B illustrates an operation of the CR unit 103 obtaining X-ray radiographic images of a subject in a decubitus position;

DETAILED DESCRIPTION OF THE EXEMPLARY EMBODIMENTS

First Embodiment

<General Arrangement of X-ray Hybrid Diagnosis System>

Figure 1:
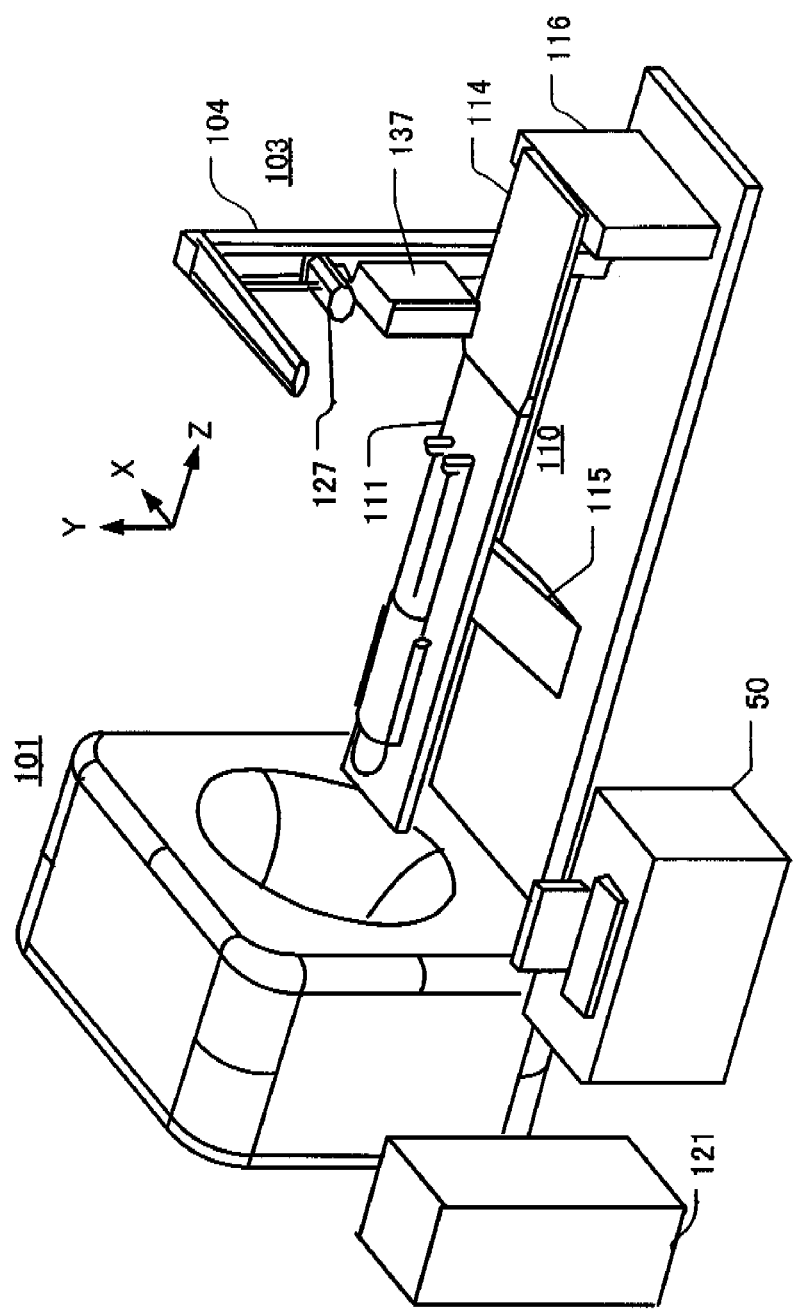
FIG. 1 is a perspective view showing a setup of an X-ray hybrid diagnosis system 100 according to a first exemplary embodiment of the present invention.

FIG. 1 is a perspective view showing a general arrangement of an X-ray hybrid diagnosis system 100 according to a first exemplary embodiment of the present invention. This system generally includes an operation console 50, a gantry 101, an X-ray power supply 121, and a CR unit 103. The operation console 50 is adapted to reconstruct an X-ray tomographic image of a subject based upon data transmitted from the gantry 101 and to display the X-ray tomographic image. The operation console 50 is also adapted to display an X-ray radiographic image based upon data transmitted from a flat panel detector 137. The X-ray power supply 121 is adapted to power an X-ray CR system and X-ray CT system The gantry 101 is a computed tomography or CT unit adapted to acquire X-ray projection data to obtain tomography images of a subject. The CR unit 103 is a computed radiography unit (digital X-ray imager) adapted to obtain X-ray radiographic images of the subject.

Not every component of the X-ray hybrid diagnosis system 100 need be placed in one and the same room. For example, the gantry 101 and the CR unit 103 may be placed in a consulting room in which patients as examinees are diagnosed, whereas the operation console 50 may be placed in an operation room for a radiographer. The X-ray power supply 121 for powering the X-ray CR system and X-ray CT system may be placed in a basement in order to free up a space in the consulting room or operation room.

The cradle 110 includes a first cradle 111 and a second cradle 114 provided on a Z-direction side (facing toward a direction indicated by an arrow Z in FIG. 1) of the first cradle 111. The first cradle 111 is movable, with a subject laid thereon in a decubitus position; i.e., the first cradle 111 can be actuated by a first cradle drive unit 115 to move toward the gantry 101. The second cradle 114 is movable; i.e., the second cradle 114 can be actuated by a second cradle drive unit 116 to translate along the Y axis toward the direction indicated by the arrow Y (the direction will hereinafter be referred to as "Y-axis direction" or "+Y-axis direction") as well as to tilt to any desired angles. The CR unit 103 is disposed at one side of the cradle 110 near an interface between the first cradle 111 and the second cradle 114.

Figure 2:
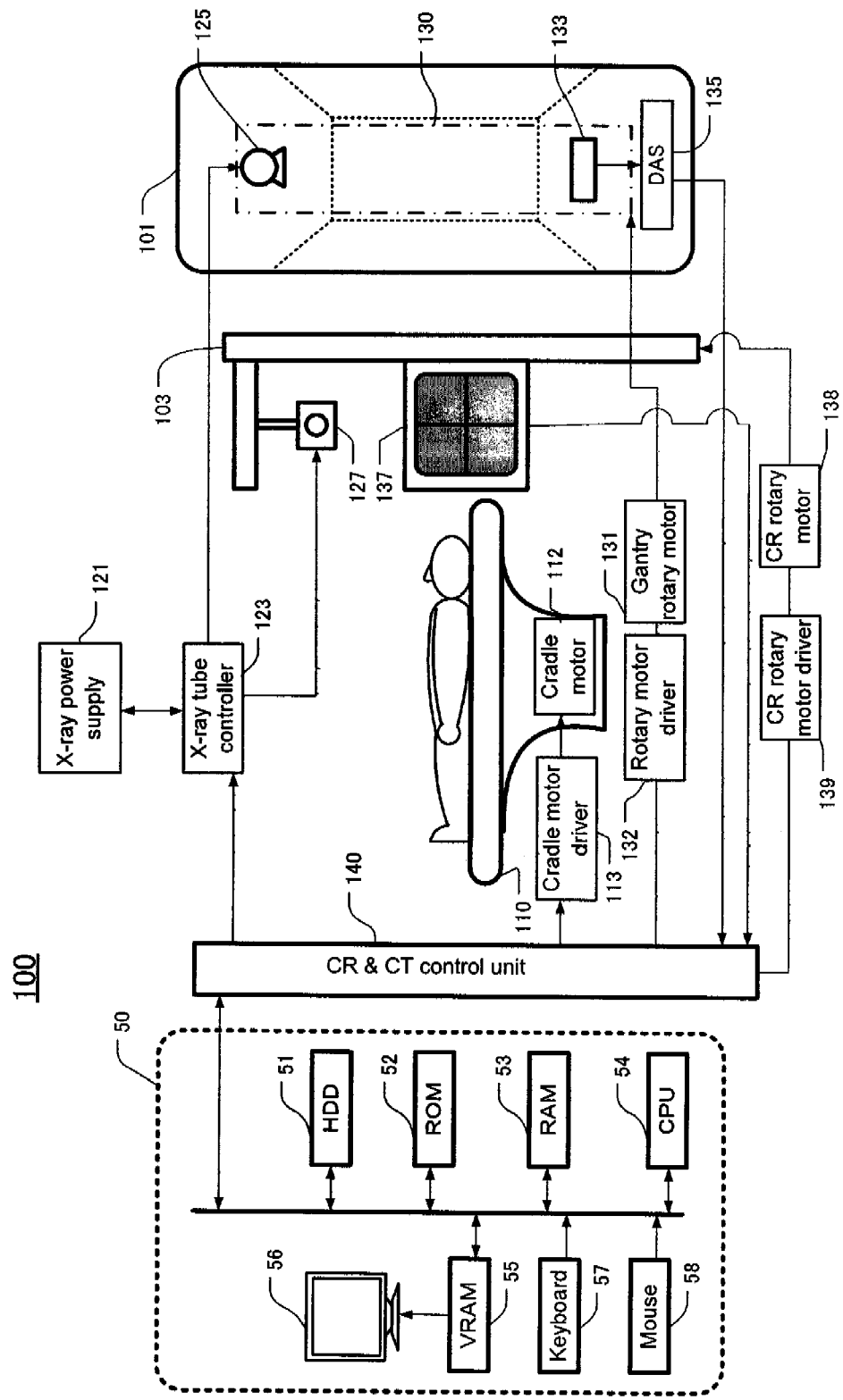
FIG. 2 is a block diagram representing the X-ray hybrid diagnosis system 100.

FIG. 2 is a block diagram representing an arrangement of the X-ray hybrid diagnosis system 100 according to one exemplified embodiment of the present invention. The gantry 101 and the CR unit 103 are communicatively coupled with a CR & CT control unit 140 and various other devices which will be described later, and are configured to operate under control of the CR & CT control unit 140.

Inside the gantry 101 are provided an X-ray tube 125 for producing X rays, an X-ray tube controller 123 connected with the X-ray tube 125, a collimator (not shown) for limiting a range of irradiation of X rays, a control motor (not shown) connected with the collimator for regulating a dimension of an opening (slit or aperture) of the collimator, and other components. X rays that have passed through the collimator form a fan-shaped beam (so-called "fan beam") of X rays, which beam is broad in a plane perpendicular to an axis of rotation of the gantry 101 (revolution of the X-ray tube 125) and narrow in a direction parallel to the axis of rotation of the gantry 101.

Also provided inside the gantry 101 is an X-ray detection unit 133, which includes multiple rows of detection channels each having a plurality of detectors. Each detector has a length depending upon a fan angle (normally 60° or so). The detection channels are arranged in a direction (element direction) along the Z-axis direction. The X-ray detection unit 133 is, for example, made up of a scintillator and a photodiode used in combination.

The gantry 101 includes at least one data acquisition unit or DAS (standing for data acquisition system) 135 which acquires projection data from outputs of the detection channels. The number of the data acquisition unit(s) 135 may be one or more (e.g., four, eight, sixteen or thirty two), and each data acquisition unit 135 is connected with the X-ray detection unit 133. For example, the gantry 101 including four data acquisition units 135, which is normally called "4DAS", includes the detection channels arranged in four rows in the element direction, and can obtain four slice images in one cycle of revolution of the X-ray tube 125. The X-ray tube 125 and the X-ray detection unit 133 are disposed in opposite positions in the gantry 101 such that a hollow space for accommodating a subject is left between the X-ray tube 125 and the X-ray detection unit 133. The X-ray tube 125 and the X-ray detection unit 133 are attached to a rotor 130 so that the X-ray tube 125 and the X-ray detection unit 133 revolve around the subject while maintaining the opposed positions relative to each other. A gantry rotary motor 131 and a gantry rotary motor driver 132 are connected with the rotor 130, and the rotor 130 is regulated by the gantry rotary motor driver 132 to make one rotation in any speeds needed.

The X-ray hybrid diagnosis system 100 provides user-selectable options of operation modes: a full-scan mode in which images are reconstructed from projection data of 360° and a half-scan mode in which images are reconstructed from projection data of 180° plus one unit fan angle. Each scan mode offers its own peculiar advantage: high-quality tomographic images can be reconstructed in the full-scan mode, while increased scanning speed, which can be obtained at the expense of some resolution of the tomographic images, in the half-scan mode leads to reduction in exposure of a subject to radiation.

The CR unit 103 includes an X-ray tube 127 for producing X rays and a collimator (not shown) having an opening for limiting a range of irradiation of X rays produced in the X-ray tube 127. The X-ray tube controller 123 is connected with the X-ray tube 127. Also provided in the CR unit 103 is a flat panel detector 137 adapted to receive X-rays from the X-ray tube 127. The flat panel detector 137 includes a two-dimensional panel sensor comprised, for example, of a scintillator and a sensor such as a CCD sensor, a MOS sensor or a CMOS sensor.

The position of the X-ray tube 127 and the flat panel detector 137 can be adjusted through six degrees of freedom, in accordance with the posture (standing, sitting or decubitus position) of the subject or the portion to be radiographed of the subject. For that purpose, a CR rotary motor 138 and a CR rotary motor driver 139 are connected with the CR unit 103.

The subject laid on the first cradle 111 in a decubitus position is moved in the body-axial direction of the subject (i.e., Z-axis direction) by a cradle motor (first cradle motor) 112. The cradle motor 112 is actuated by a cradle motor driver (first cradle motor driver) 113. The second cradle 114 (see FIG. 1 and other drawings) which can be mated to the first cradle 111 is provided and actuated by a motor (second cradle motor that is not shown) with a motor driver (second cradle motor driver that is not shown).

Additionally, an electrocardiograph for transducing a heartbeat into an electric signal may be attached if necessary to the subject in order to check the heartbeat conditions of the subject. By providing the signal from the electrocardiograph to the CT & CR control unit 140, irradiation of X rays can be carried out in accordance with the heartbeat conditions of the subject.

The CT & CR control unit 140 is communicatively coupled with the operation console 50. Responsive to instructions from the operation console 50, various control signals are transmitted to the X-ray tube controller 123, the cradle motor driver 113 and the rotary motor driver 132 as well as an opening regulator motor driver (not shown) and the like. Data acquired by the data acquisition unit 135 are transmitted to the operation console 50 in which images are reconstructed and tomographic images are displayed. Similarly, data obtained by the flat panel detector 137 are transmitted to the operation console 50 in which radiographic images are displayed.

The operation console 50 is typically embodied in a workstation, as illustrated in FIG. 2, which mainly includes a ROM 52 storing a boot program and the like, a RAM 53 serving as a main memory and a CPU 54 executing instructions for controlling the entire system.

A hard disk drive or HDD 51 is provided in the operation console 50 to store not only an operating system but also image-processing programs for providing various instructions given to the gantry 101 and the CR unit 103 and instructions to display radiographic images based upon data received from the flat panel detector 137, as well as image-processing programs for reconstructing and displaying X-ray tomographic images based upon data received from the data acquisition unit 135. A VRAM 55 is a memory in which image data to be displayed are deployed, that is, the image data, etc. can be deployed in the VRAM 55 and thereby displayed in a monitor 56. Operators use a keyboard 57 and a mouse 58 to perform a variety of operations and manipulations.

CR Unit 103 Setup>

Figure 3:
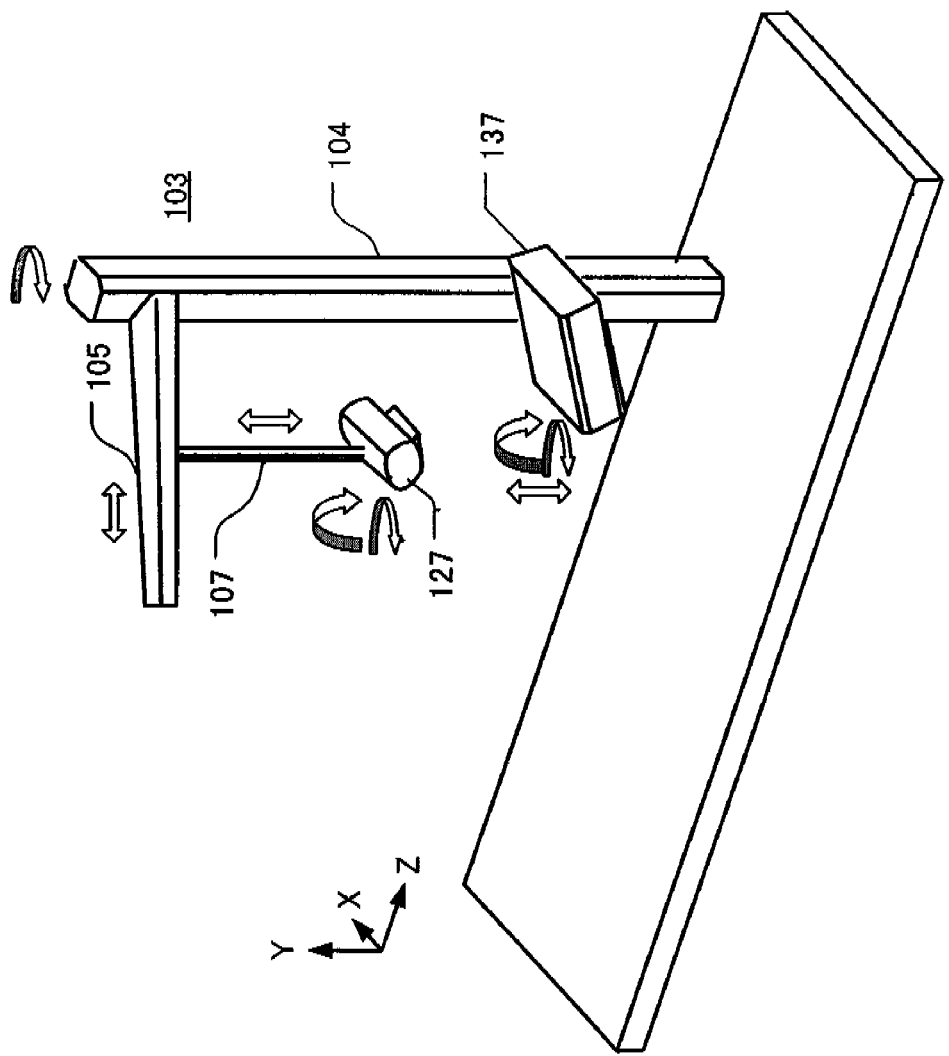
FIG. 3 is a perspective view showing a setup of a CR unit 103.

FIG. 3 is a perspective view showing a setup of the CR unit 103. A frame of the CR unit 103 is comprised of a rotation support post 104, a swivel arm 105 provided at an upper portion of the rotation support post 104, and an extendable arm 107 suspended from the swivel arm 105. The X-ray tube 127 is provided at an end of the extendable arm 107 in a manner that allows the X-ray tube 127 to rotate via a ball joint mechanism. The flat panel detector 137 is provided at a midpoint of the rotation support post 104 in a manner that allows the flat panel detector 137 to move vertically and rotate. Accordingly, X-ray radiographic images can be obtained from various angles in accordance with the posture of the subject or the portion to be radiographed of the subject.

<Cradle Setup>

Figure 4:
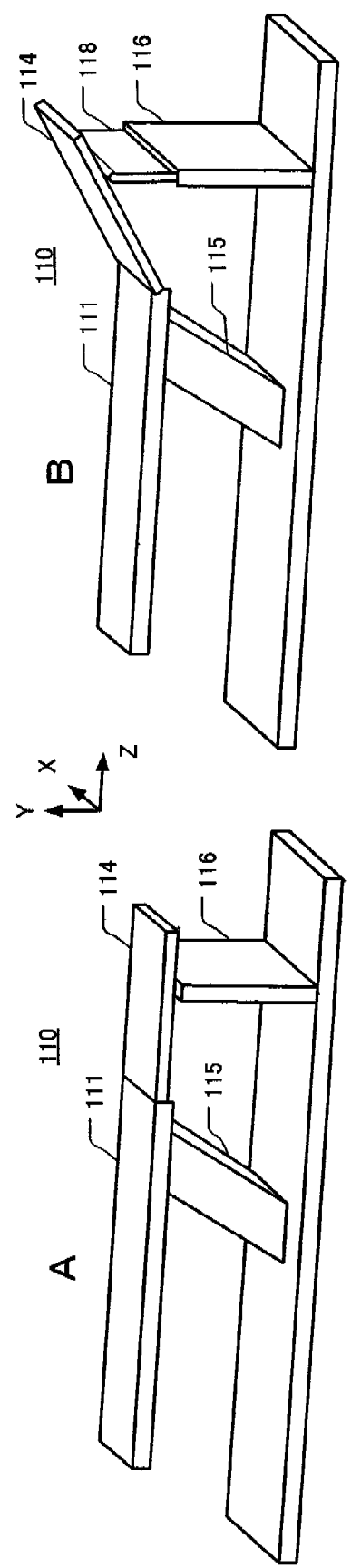
FIGS. 4A and 4B are perspective views showing a variable setup of a cradle.

FIGS. 4A and 4B are perspective views showing a variable setup of the cradle 110. Opposed ends of the first cradle 111 and the second cradle 114 are not adhered to each other but only abutted with each other. Thus, the first cradle 111 alone can independently move in the Z-axis direction, and the second cradle 114 as well can independently move. The second cradle 114 includes a driving arm 118 that is rendered extendable so that the second cradle drive unit 116 can extend or contract the driving arm 118 to tilt the second cradle 114. A driving motor is provided at an end of the driving arm 118 so that the second cradle 114 can be moved in the Y-axis direction.

The first cradle 111 has enough length to allow an ordinary subject to lie thereon without any problems. The second cradle 114 has enough length to perform a function auxiliary to the first cradle 111. Contact sensors (not shown) are attached to the ends of the first and second cradles 111 and 114, as a safeguard so that the body of an examinee as a patient is not caught in between them. The first and second cradles 111 and 114 are both made of X-ray transparent plastic material.

<Implementation of X-ray Imaging According to First Embodiment>

Figure 5:
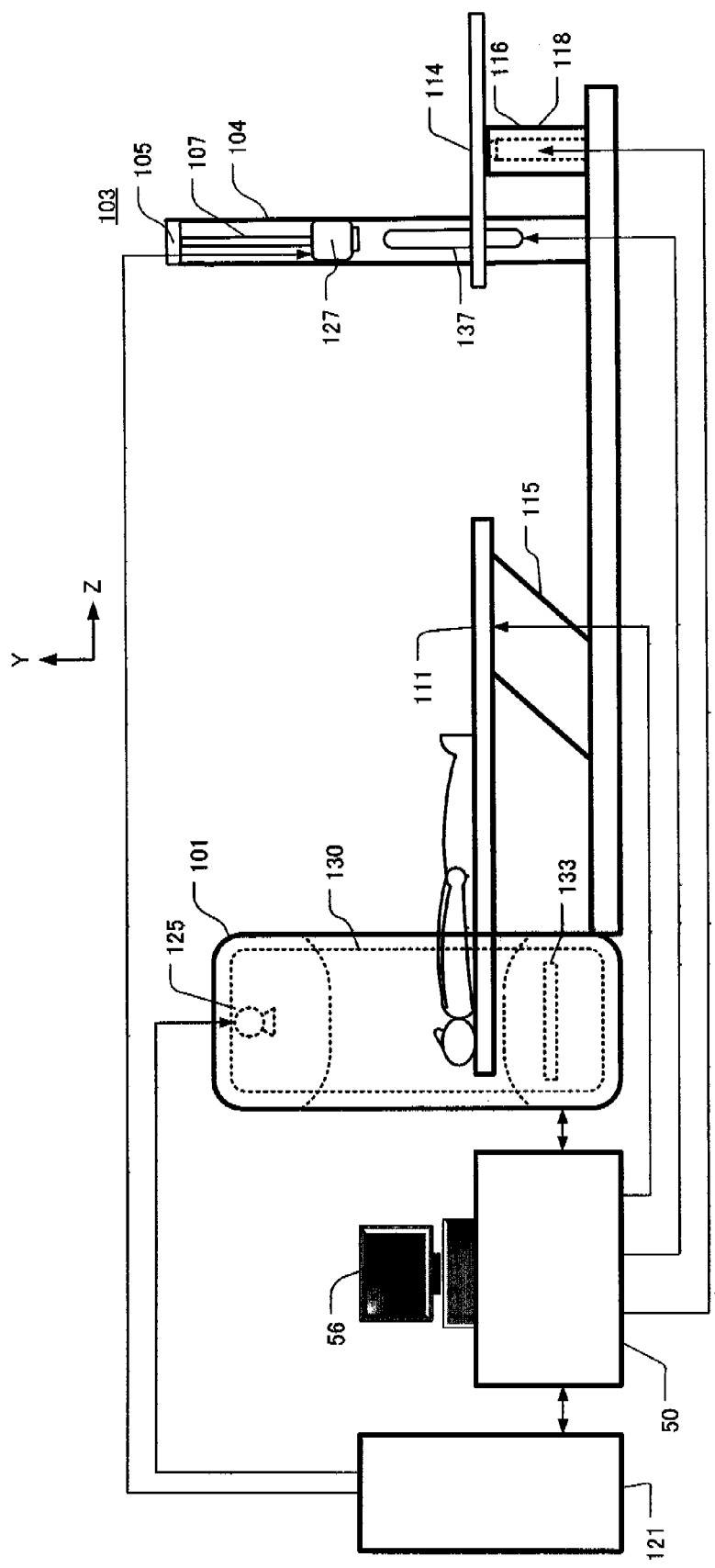
FIG. 5 illustrates an operation of a gantry 101 as a CT unit obtaining X-ray tomographic images of a subject in a decubitus position.
Figure 6:
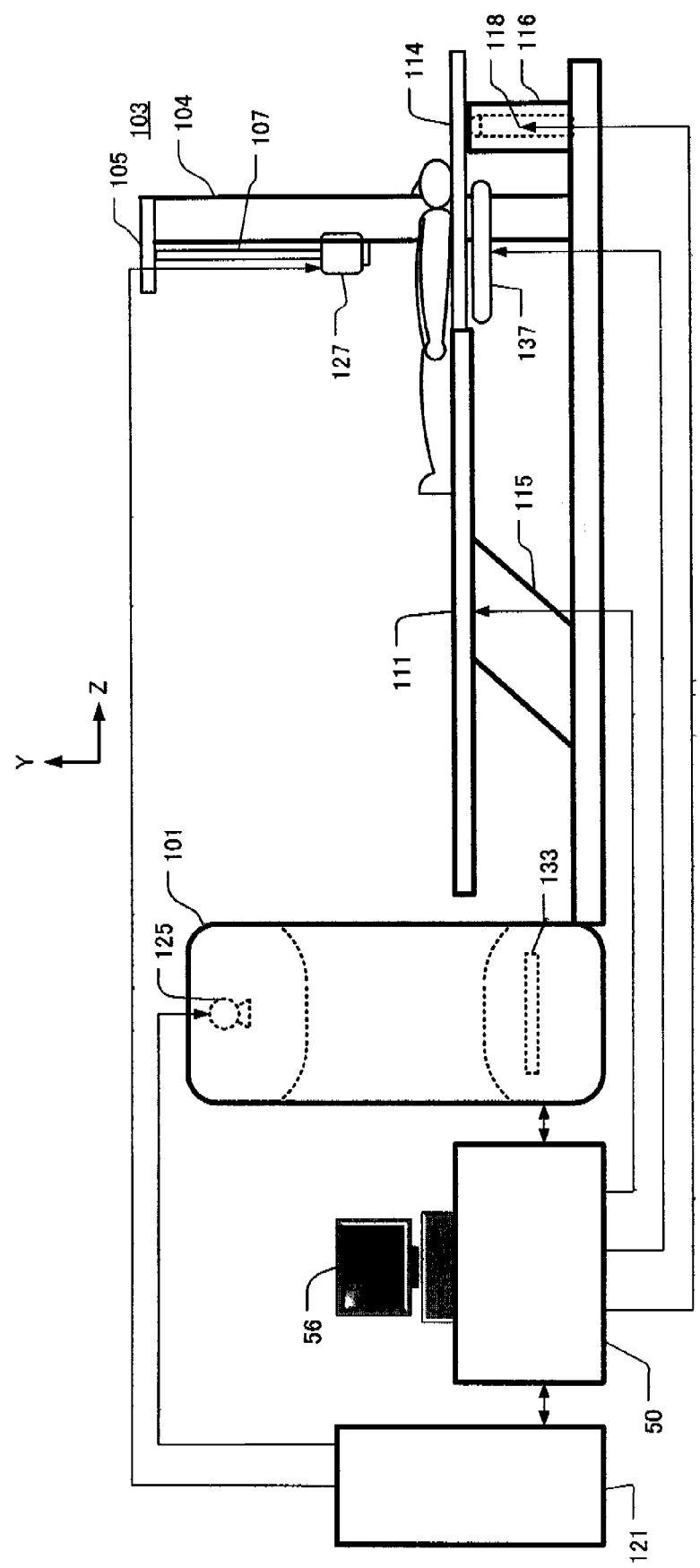
FIG. 6 illustrates an operation of the CR unit 103 obtaining X-ray radiographic images of a subject in a decubitus position.
Figure 7:
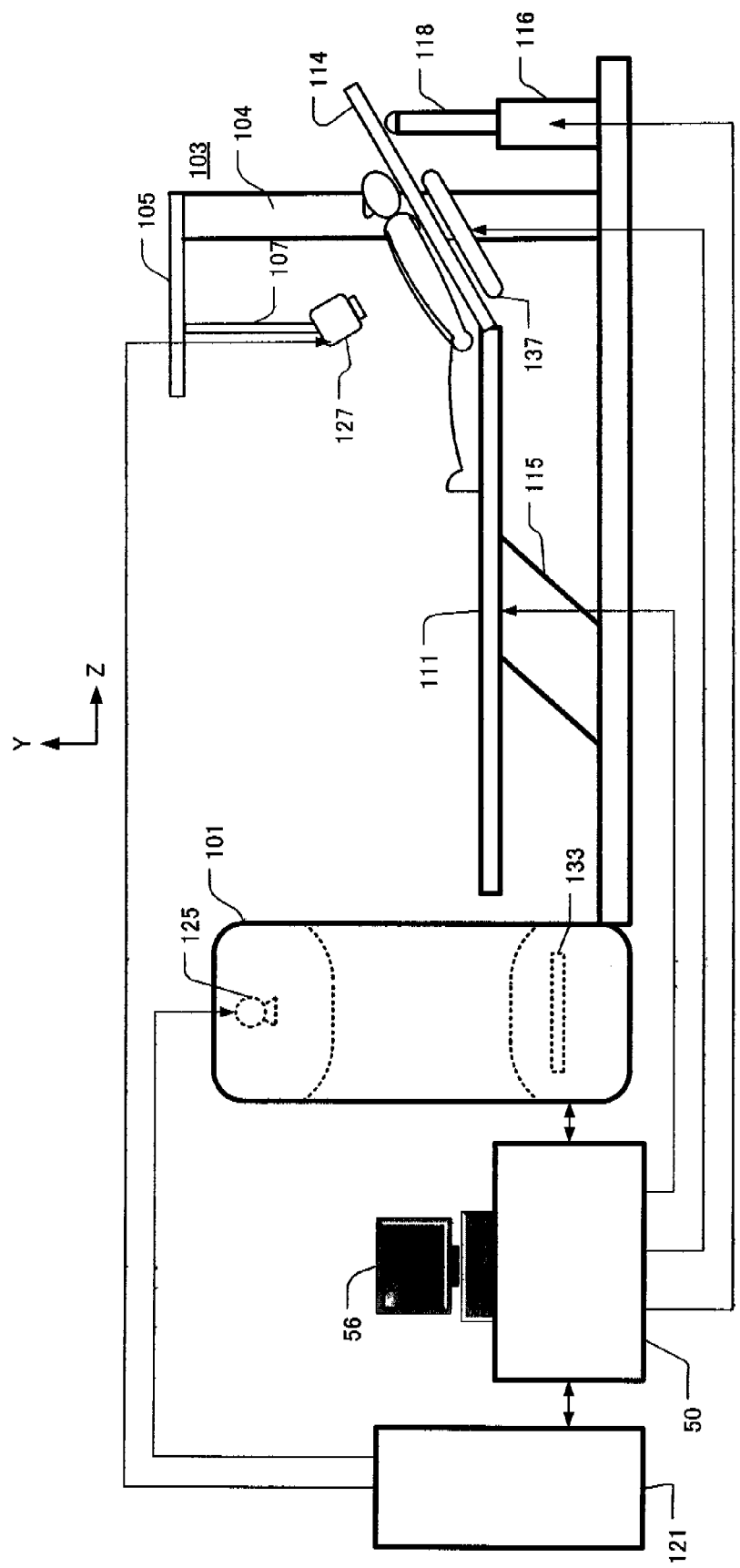
FIG. 7 illustrates an operation of the CR unit 103 obtaining X-ray radiographic images of a subject in a sitting position.
Figure 8:
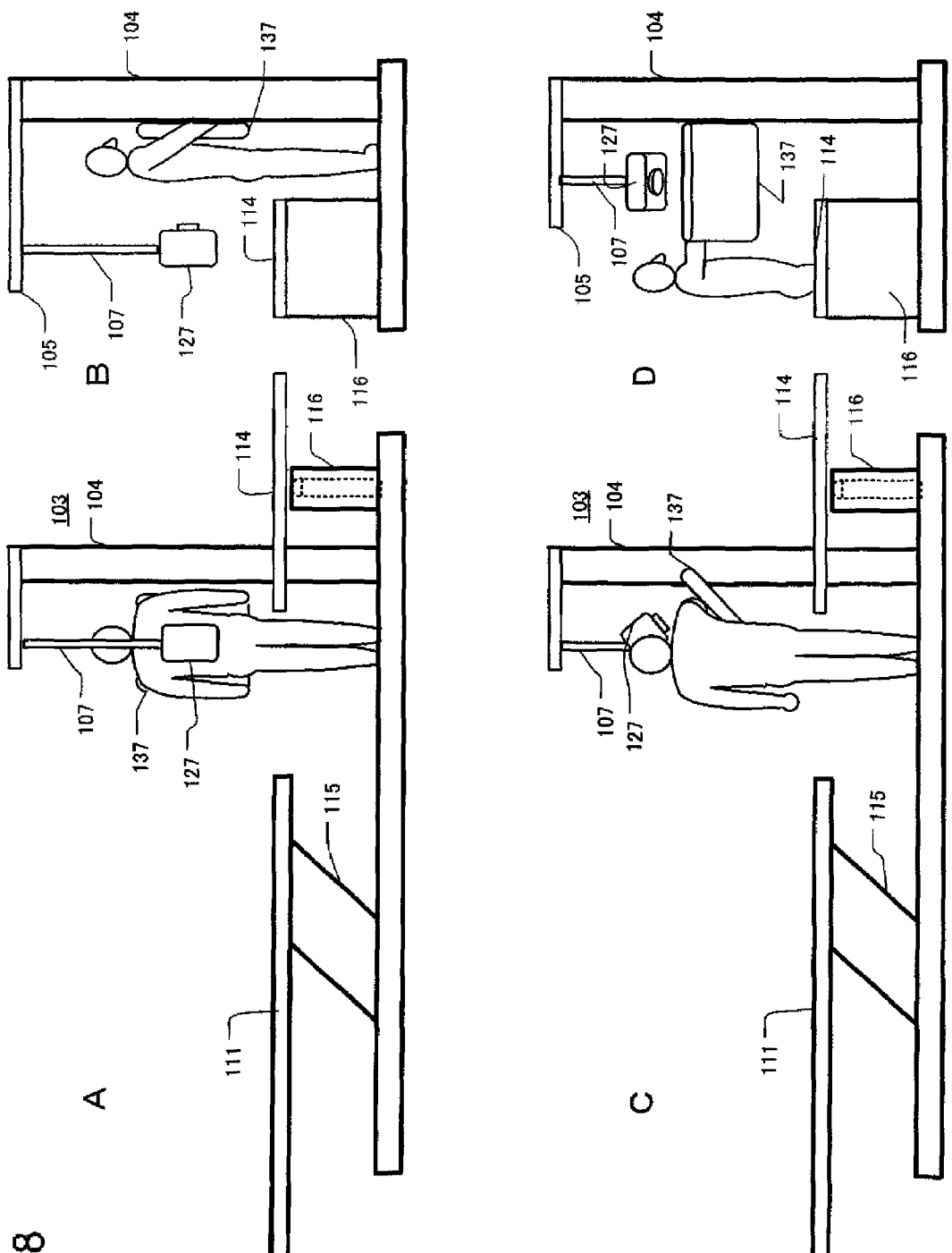
FIGS. 8A-8D illustrate a series of operations of the CR unit 103 obtaining X-ray radiographic images of a subject in a standing position, where

FIGS. 5 through 8D illustrate operations of the X-ray hybrid diagnosis system 100 obtaining X-ray images according to the first embodiment. FIG. 5 illustrates an operation of the gantry 101 as a CT unit obtaining X-ray tomographic images of a subject in a decubitus position. FIG. 6 illustrates an operation of the CR unit 103 obtaining X-ray radiographic images of a subject in a decubitus position. FIG. 7 illustrates an operation of the CR unit 103 obtaining X-ray radiographic images of a subject in a sitting position. FIGS. 8A-8D illustrate a series of operations of the CR unit 103 obtaining X-ray radiographic images of a subject in a standing position. FIG. 8A is a front elevation for showing an operation of obtaining a chest image of the subject, and FIG. 8B is a side elevation of FIG. 8A. FIG. 8C is a front elevation for showing an operation of obtaining an upper-arm image of the subject, and FIG. 8D is a side elevation of FIG. 8C.

FIG. 5 shows a state in which a subject laid on the first cradle 111 is moving from his/her head into the hollow space in the gantry 101. An operator such as a radiographer inputs radiographic conditions or the like into the operation console 50 using the keyboard 57 and/or the mouse 58. In response to an instruction from the operation console 50, the rotor 130 in the gantry 101 is actuated to rotate and the first cradle 111 moves at a predetermined speed. Accordingly, so-called "helical scan" is performed. The X-ray tube 125 disposed on the rotor 130 in the gantry 101 is powered by the X-ray power supply 121. On the other hand, the CR unit 103 and the second cradle drive unit 116 are not supplied with any currents such as a drive signal, except for standby current, and the CR unit 103 and the second cradle 114 are positioned in their initial positions. The subject can be move from his/her foot into the hollow space in the gantry 101 as well.

FIG. 6 shows a state in which a subject is prepared in a decubitus position for obtaining X-ray radiographic images of his/her chest. The operator inputs radiographic conditions or the like into the operation console 50 using the keyboard 57 and/or the mouse 58. In response to an instruction from the operation console 50, the X-ray tube 127 and the flat panel detector 137 are actuated to move and rotate into predetermined positions. The second cradle 114 is also actuated to move into a predetermined position. The X-ray tube 127 is powered by the X-ray power supply 121. On the other hand, the gantry 101 and the first cradle drive unit 115 are not supplied with any currents such as a drive signal, except for standby current, and the rotor 130 and the first cradle 110 are positioned in their initial positions. The X-ray radiographic image of any other part can be obtained as well.

FIG. 7, like FIG. 6, shows a state in which a subject is prepared for obtaining X-ray radiographic images of his/her chest. FIG. 7 is however different from FIG. 6 in that the subject is in a sitting position. In response to an instruction from the operation console 50, the X-ray tube 127 and the flat panel detector 137 are actuated to move and rotate into predetermined positions. The second cradle 114 is also actuated to move and tilt into a predetermined position. The X-ray tube 127 is powered by the X-ray power supply 121. On the other hand, the gantry 101 and the first cradle drive unit 115 are not supplied with any currents such as a drive signal, except for standby current, and the rotor 130 and the first cradle 110 are positioned in their initial positions.

FIGS. 8A and 8B show a state similar to those shown in FIGS. 6 and 7 in which X-ray radiographic images of subject's chest are being obtained. FIGS. 8A and 8B are however different from FIG. 6 or 7 in that the subject is in a standing position. In response to an instruction from the operation console 50, the X-ray tube 127 and the flat panel detector 137 are actuated to move and rotate into predetermined positions. The second cradle 114 is not to be used, and thus positioned in its initial position. The X-ray tube 127 is powered by the X-ray power supply 121.

FIGS. 8C and 8D show a state in which X-ray radiographic images of examinee's upper arm are being obtained. In response to an instruction from the operation console 50, the X-ray tube 127 and the flat panel detector 137 are actuated to move and rotate into predetermined positions. The second cradle 114 is not to be used, and thus positioned in its initial position.

Second Embodiment

<General Arrangement of X-ray Hybrid Diagnosis System>

Figure 9:
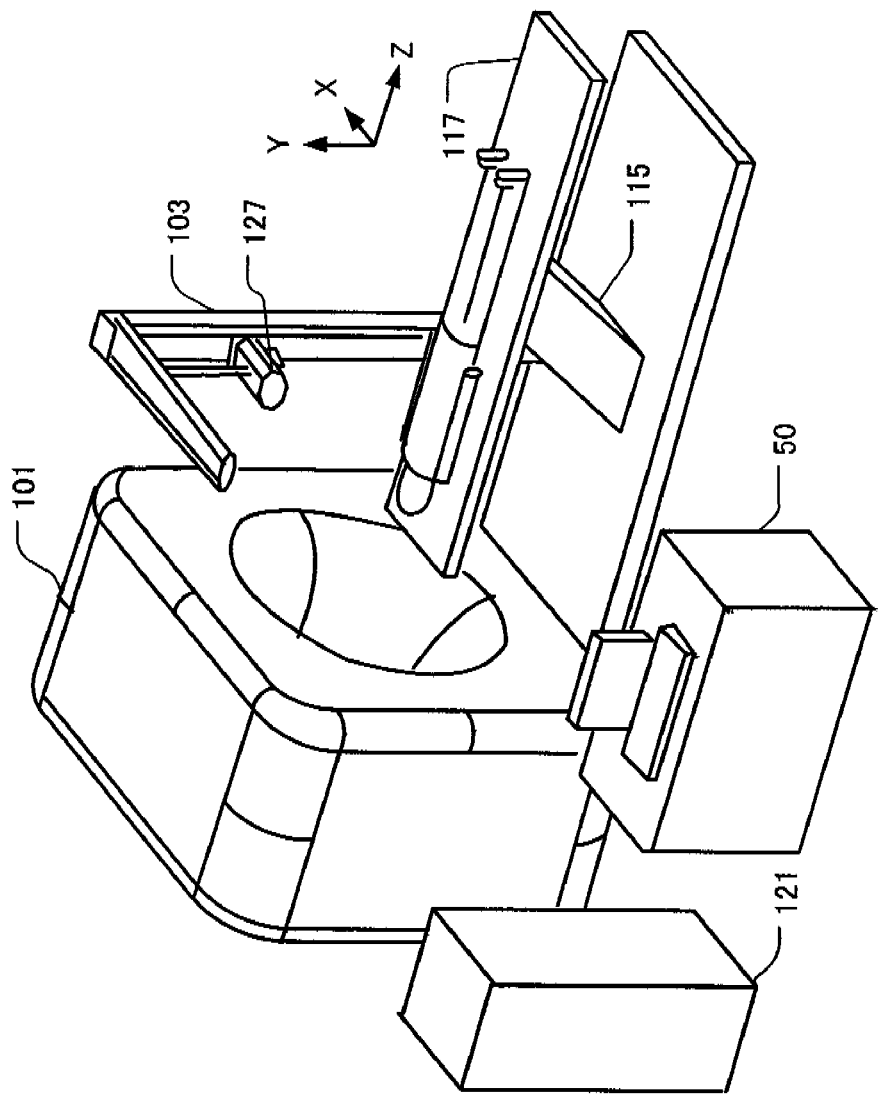
FIG. 9 is a perspective view showing a setup of an X-ray hybrid diagnosis system 100 according to a second exemplary embodiment of the present invention.

FIG. 9 is a perspective view showing a general arrangement of an X-ray hybrid diagnosis system 100 according to a second exemplary embodiment of the present invention. This embodiment is substantially different from the first embodiment as described with reference to FIG. 1 in that the X-ray hybrid diagnosis system 100 according to the second embodiment includes no second cradle, and a flat panel detector is incorporated in a cradle. Such difference will become a focus of the following discussion.

A third cradle 117 is movable, with a subject laid thereon in a decubitus position, toward the gantry 101. The CR unit 103 is disposed at one side of the third cradle 117.

<Cradle Structure>

FIGS. 10A through 10C show a structure of the third cradle 117. FIG. 10A is a perspective view of the third cradle 117. FIG. 10B is a phantom showing the third cradle 117 in cross section. FIG. 10C is a tomographic view taken along line C-C of FIG. 10B. As shown in FIG. 10A, the third cradle 117 has a hollow space and made of X-ray transparent material such as plastic. In this hollow space is provided a flat panel detector 70 that is movable bidirectionally along the Z axis as indicated by an arrow. The third cradle 117 can move in the Z-axis directions on a table, and can be raised upright by a raising drive unit 119, as will be described with reference to FIG. 12A, comprised of an air cylinder or the like.

As shown in FIGS. 10B and 10C, guide rails 77 are provided in the hollow space of the third cradle 117 so that the flat panel detector 70 can smoothly move in a specific direction. The guide rails 77 are made of X-ray transparent hard plastic or the like so that the guide rails 77 do not cast the shadow on X-ray CT scanned images. The length of the guide rails 77 has the enough length in the Z-axis direction. Four tires 75 corresponding to the guide rails 77 are provided on the flat panel detector 70. A driving motor 73 is provided in the flat panel detector 70 to drive the tires 75. A two-dimensional panel sensor 71 is provided on an X-Z plane in the flat panel detector 70. The two-dimensional panel sensor 71 is comprised for example of a scintillator and a sensor, such as CCD sensor, MOS sensor, or CMOS sensor. When the X-ray CT scan is performed, the flat panel detector 70 has been moved to a retracted position that is at the end of the third cradle 117 facing toward the +Z-axis direction. Therefore, the two-dimensional panel sensor 71, driving motor 73 and tires 75 may contain materials, such as metal, which are not completely transparent to X rays, without any problem.

A transparent window 78 made of plastic is formed in a part of a top plate of the third cradle 117. This allows an operator to visually check where the flat panel detector 70 is located in actuality. The transparent window 78 may preferably be provided near a side of the top plate of the third cradle 117 so that the position of the flat panel detector 70 can be checked even when the subject is laid on the third cradle 117 in a decubitus position. A center line is marked on the top face of the flat panel detector 70 so that the center of the two-dimensional panel sensor 71 along the length in the Z-axis direction can be seen through the transparent window 78.

In order to supply power to the two-dimensional panel sensor 71 and the driving motor 73, a power cable (not shown) is provided between the flat panel detector 70 and the third cradle 117, and likewise a signal line through which a signal is output from the two-dimensional panel sensor 71 is provided between the flat panel detector 70 and the third cradle 117. As shown in FIGS. 10B and 10C, the driving motor 73 is arranged in the flat panel detector 70 in this embodiment, but may alternatively be arranged in the third cradle 117. Further provided in the third cradle 117 is, as shown in FIG. 10C, a position sensor 79 for detecting where (in the Z-axis direction) in the third cradle 117 the flat panel detector 70 is located. In an embodiment where the driving motor 73 is a stepping motor or the like, the position of the flat panel detector 70 can be detected if the position of the flat panel detector 70 is initialized every time upon startup, and thus such a position sensor 79 would not necessarily required.

<Implementation of X-ray Radiography According to Second Embodiment>

Figure 12:
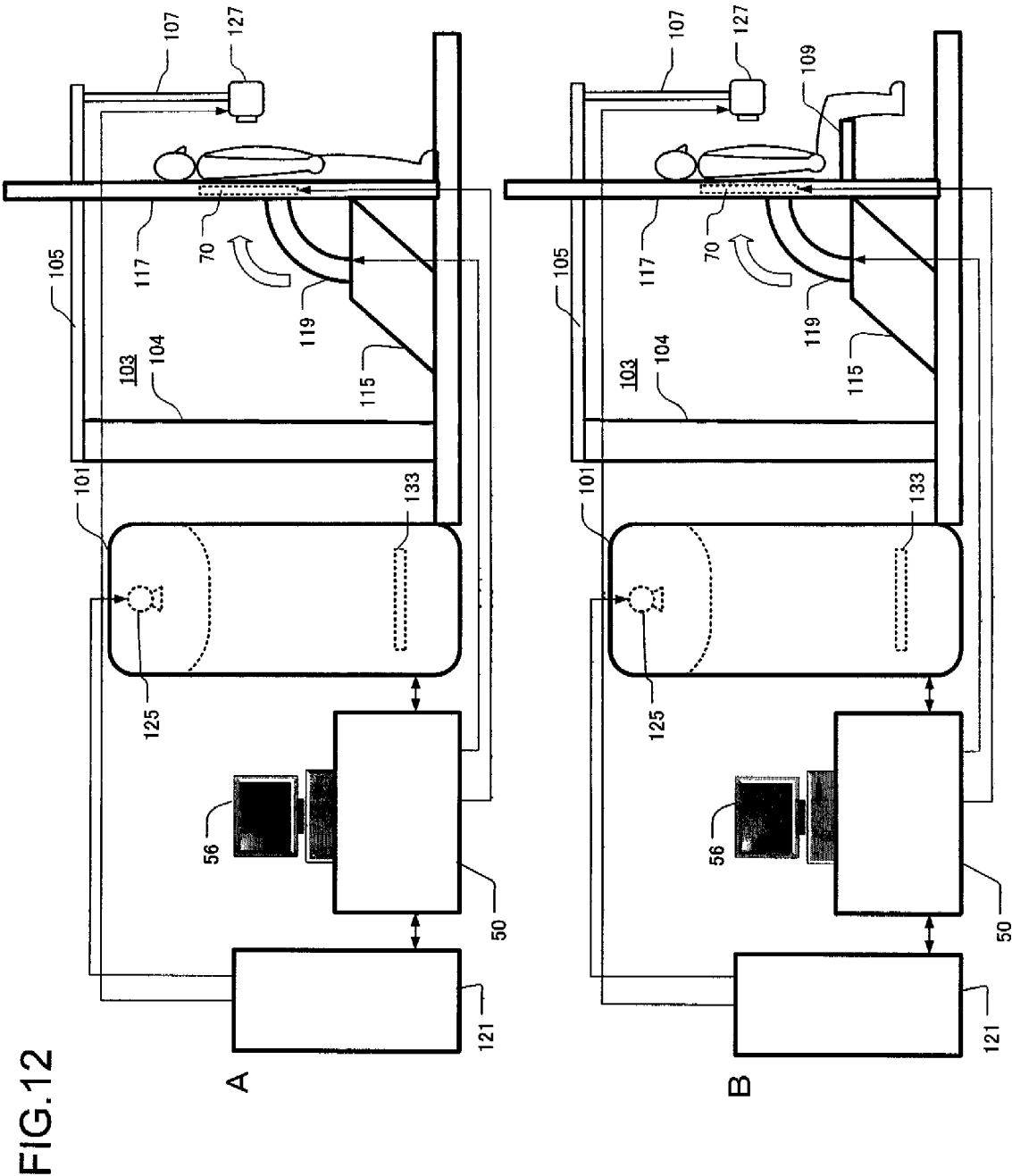
FIG. 12A illustrates an operation of the CR unit 103 obtaining X-ray radiographic images of a subject in a standing position.
FIG. 12B illustrates an operation of the CR unit 103 obtaining X-ray radiographic images of a subject in a sitting position.

FIGS. 11A, 11B, 12A and 12B illustrate operations of obtaining X-ray images in the X-ray hybrid diagnosis system 100 according to the second embodiment. FIG. 11A illustrates an operation of the gantry 101 as the CT unit obtaining X-ray tomographic images of a subject in a decubitus position. FIG. 11B illustrates an operation of the CR unit 103 obtaining X-ray radiographic images of a subject in a decubitus position. FIG. 12A illustrates an operation of the CR unit 103 obtaining X-ray radiographic images of a subject in a standing position in the CR unit 103. FIG. 12B illustrates an operation of the CR unit 103 obtaining X-ray radiographic images of a subject in a sitting position.

FIG. 11A shows a state in which a subject is moving from his/her head into the hollow space in the gantry 101, so as to be subjected to the X-ray CT scan. An operator such as a radiographer inputs radiographic conditions or the like into the operation console 50 using the keyboard 57 and/or the mouse 58. In response to an instruction from the operation console 50, the rotor 130 in the gantry 101 is actuated to rotate and the third cradle 117 moves at a predetermined speed. Accordingly, so-called "helical scan" is performed. The X-ray tube 125 disposed on the rotor 130 in the gantry 101 is powered by the X-ray power supply 121. During the helical scan or other type of X-ray CT scan, the flat panel detector 70 could be disposed in a range through which X-ray beams transmits until the beams enter the X-ray detection unit 133, and would disadvantageously form a shade. Therefore, the flat panel detector 70 is in a retracted position at an end of the third cradle 117 in the +Z-axis direction. The CR unit 103 and the flat panel detector 70 are not supplied with any currents such as a drive signal, except for standby current. The subject can be move from his/her foot into the hollow space in the gantry 101 as well.

FIG. 11B shows a state in which a subject is in a decubitus position so that his/her chest is to be radiographed by the CR unit 103. An operator such as a radiographer inputs radiographic conditions or the like into the operation console 50 using the keyboard 57 and/or the mouse 58. In response to an instruction from the operation console 50, the X-ray tube 127 is moved, rotated and placed in a predetermined position, and the flat panel detector 70 is moved to a predetermined position. The relative position of the X-ray tube 127 and the flat panel detector 70 is displayed in the monitor 56 of the operation console 50. The X-ray tube 127 is powered by the X-ray power supply 121. On the other hand, the gantry 101 is not supplied with any currents such as a drive signal, except for standby current, and the rotor 130 is positioned in their initial positions. The radiograph can be of any parts other than chest as well.

FIG. 12A shows a state, like that of FIG. 11B, in which a subject is to be radiographed by the CR unit 103, though the examiner's body is, unlike that of FIG. 11A, in a standing position. In response to an instruction from the operation console 50, first, the third cradle 117 is moved to its initial position, and a raising drive unit 119 such as an air cylinder or an electric motor is actuated to raise the third cradle 117 into an upright posture. Moreover, in response to an instruction from the operation console 50, the X-ray tube 127 and the flat panel detector 70 are moved to a predetermined position.

FIG. 12B shows a state in which a subject is to be radiographed by the CR unit 103, though the examiner's body is, unlike those of FIGS. 11B and 12A, in a sitting position. An operator attaches a seat, which has been prepared in advance, to the third cradle 117, after the third cradle 117 is raised into an upright posture as discussed above with reference to FIG. 12A. In response to an instruction from the operation console 50, the X-ray tube 127 and the flat panel detector 70 are moved to a predetermined position. The X-ray tube 127 is powered by the X-ray power supply 121.

<<Operation of X-ray Hybrid Diagnosis System>>
<Scan Mode>

Scanning operations in the X-ray hybrid diagnosis system 100 may be performed in one of several (generally four) scan types provided as options.

Figure 13:
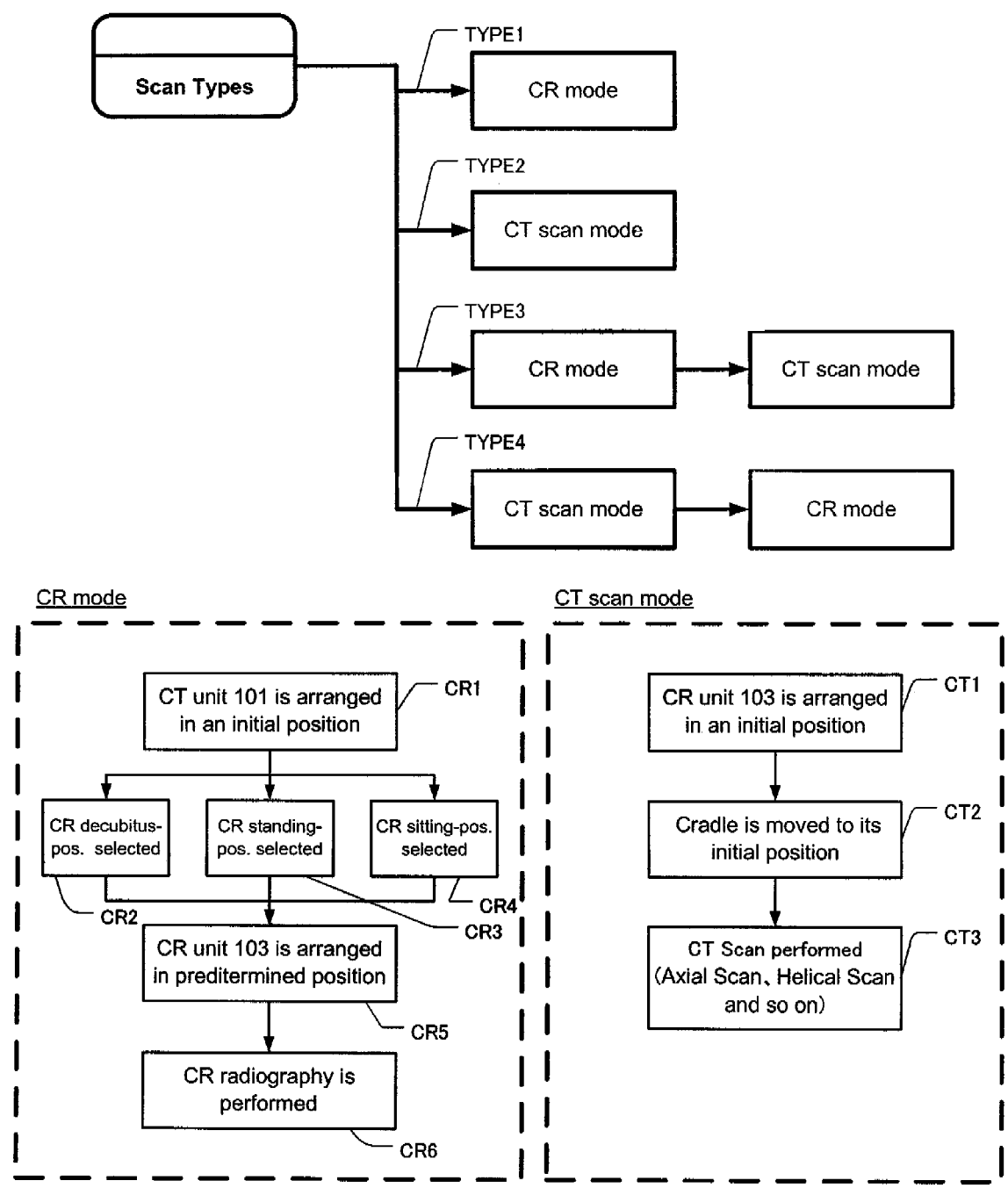
FIG. 13 shows a variety of scan types which are illustrated by way of explanation.

As shown in FIG. 13, the scan types include: TYPE 1 in which only CR is performed (CR mode); TYPE 2 in which only CT scan is performed (CT scan mode); TYPE 3 in which CR is followed by CT scan; and TYPE 4 in which CT scan is followed by CR.

The operation performed in CR mode is substantially the same as the scanning operation performed by a single CR unit. The next discussion will focus on the CR mode. In step CR1, the gantry 101 as a CT unit is arranged in an initial position. To be more specific, the X-ray tube 125 and the X-ray detection unit 133 in the gantry 101 are returned to their initial positions. In the first embodiment, the first cradle 111 is returned to its initial position. In the second embodiment, the third cradle 117 is returned to its initial position on a temporary basis.

In step CR2, decubitus-position radiography is selected, and an instruction from the operation console 50 invokes step CR5. In the first embodiment, the second cradle 114 is moved and positioned horizontally with its top face being flush and in contact with that of the first cradle 111. The X-ray tube 127 and the flat panel detector 137 of the CR unit 103 are moved to positions corresponding respectively to the portion to be radiographed. This state is shown for example in FIG. 6. However, the first cradle drive unit 115 that supports the first cradle 111 or the second cradle drive unit 116 that supports the second cradle 114 might obstruct optimum positioning of the flat panel detector 70. Therefore, the subject may be placed and laid flat between the first cradle drive unit 115 and the second cradle drive unit 116 to allow the flat panel detector 70 to be positioned properly under the portion to be radiographed of the subject. In the second embodiment, the third cradle 117 remains in its initial position, while the X-ray tube 127 and the flat panel detector 70 of the CR unit 103 are moved. This state is shown for example in FIG. 11B.

In step CR3, CR standing-position radiography is selected, and an instruction from the operation console 50 invokes step CR5. In the first embodiment, the first cradle 111 and the second cradle 114 are moved to their initial positions, respectively. The subject is thus allowed to stand between the first cradle 111 and the second cradle 114. Then, the X-ray tube 127 and the flat panel detector 137 of the CR unit 103 are moved to positions corresponding respectively to the portion to be radiographed. This state is shown for example in FIG. 8. In the second embodiment, the third cradle 117 is raised upright from its initial position by the raising drive unit 119. Then, the X-ray tube 127 and the flat panel detector 70 of the CR unit 103 are moved to positions corresponding respectively to the portion to be radiographed. This state is shown for example in FIG. 12A.

In step CR4, CR sitting-position radiography is selected, and an instruction from the operation console 50 invokes step CR5. In the first embodiment, one end of the second cradle 114 is brought into contact with the first cradle 111. Then, the driving arm 118 protrudes and thrusts up the other end of the second cradle 114 to bring the second cradle 114 into a tilting posture. The subject may thus be allowed to place his/her legs on the first cradle 111 and to rest his/her upper body from the waist up against the second cradle 114. Then, the X-ray tube 127 and the flat panel detector 137 of the CR unit 103 are moved to positions corresponding respectively to the portion to be radiographed. This state is shown for example in FIG. 7. In the second embodiment, the third cradle 117 is raised upright from the initial position by the raising drive unit 119. Then, the X-ray tube 127 and the flat panel detector 137 of the CR unit 103 are moved to positions corresponding respectively to the portion to be radiographed. This state is shown for example in FIG. 12B.

In step CR6, the X-ray tube 127 is powered by the X-ray power supply 121, and a detection signal from the flat panel detector 137 or the flat panel detector 70 is sent to the operation console 50.

The next discussion will focus on the CT scan mode. The operation performed in CT scan mode is substantially the same as the scanning operation performed by a single CT unit. In step CT1, the CR unit 103 is arranged in an initial position. To be more specific, in the first embodiment, the second cradle 114 is returned to its initial position. In the second embodiment, the flat panel detector 70 in the third cradle 117 is moved to its initial position (i.e., end position in the +Z-axis direction).

In step CT2, the first cradle 111 in the first embodiment is moved to its initial position or the third cradle 117 in the second embodiment is moved to its initial position. The subject is laid upon the first or third cradle 111, 117. This state is shown for example in FIG. 5 for the first embodiment, and in FIG. 11A for the second embodiment.

In step CT3, a CT scan is carried out. The both (first and second) embodiments as described above include a plurality of scan patterns, such as a conventional scan (axial scan), a helical scan, a variable-pitch helical scan, a helical shuttle scan, etc. The conventional scan is a scanning method in which the X-ray tube 125 and the X-ray detector 133 are revolved and projection data are acquired every time the first or third cradle 111, 117 is moved at a predetermined pitch. The helical scan is a scanning method in which the first or third cradle 111, 117 is moved at a predetermined speed while the X-ray tube 125 and the X-ray detector 133 are revolving, and projection data are acquired. The variable-pitch helical scan is a method in which the first or third cradle 111, 117 is moved at varied speeds while the X-ray tube 125 and the X-ray detector 133 are revolving as in the helical scan, and projection data are acquired. The helical shuttle scan is a method in which the first or third cradle 111, 117 is reciprocated in +Z-axis and −Z-axis directions while the X-ray tube 125 and the X-ray detector 133 are revolving as in the helical scan, and projection data are acquired.

It is understood that the types, such as TYPE 3 and TYPE 4, in which the both of CR and CT scan are performed use two X-ray tubes and two X-ray detectors. Thus, when CR images and CT images are to be obtained for the same subject, a common set of the coordinates in X-axis direction and Z-axis direction may preferably but not necessarily be used for operations in the CR and CT units 103, 101. To provide a common set of coordinates, the coordinates for use in CT scan operation may be predefined with consideration given to such instances that the legs of the subject are oriented toward the +Z-axis direction or the head of the subject is oriented toward the +Z-axis direction, for example. Similarly, the coordinates for use in CR operation may be predefined with consideration given to such instances that the subject is in a standing, sitting or decubitus (in which case the legs may be oriented toward the +Z-axis direction or the head may be oriented toward the +Z-axis direction) position. With this in view, for example, the position of the body axis (longitudinal axis) of the subject laid in a decubitus position may be defined as the Z axis in the system 100, and the orientation of the head of the subject may be defined as the −Z-axis direction, so that the positions of each component of the system 100 may be converted into those plotted in a common coordinate system.

<X-ray Irradiation Control>

In the first and second embodiments of the present invention, the X-ray tube controller 123 of the X-ray hybrid diagnosis system 100 is configured to exercise control over the X-ray tube 125 for CT scan operation and the X-ray tube 127 for CR operation using a single X-ray power supply 121. The control will be described in detail below.

Figure 14:
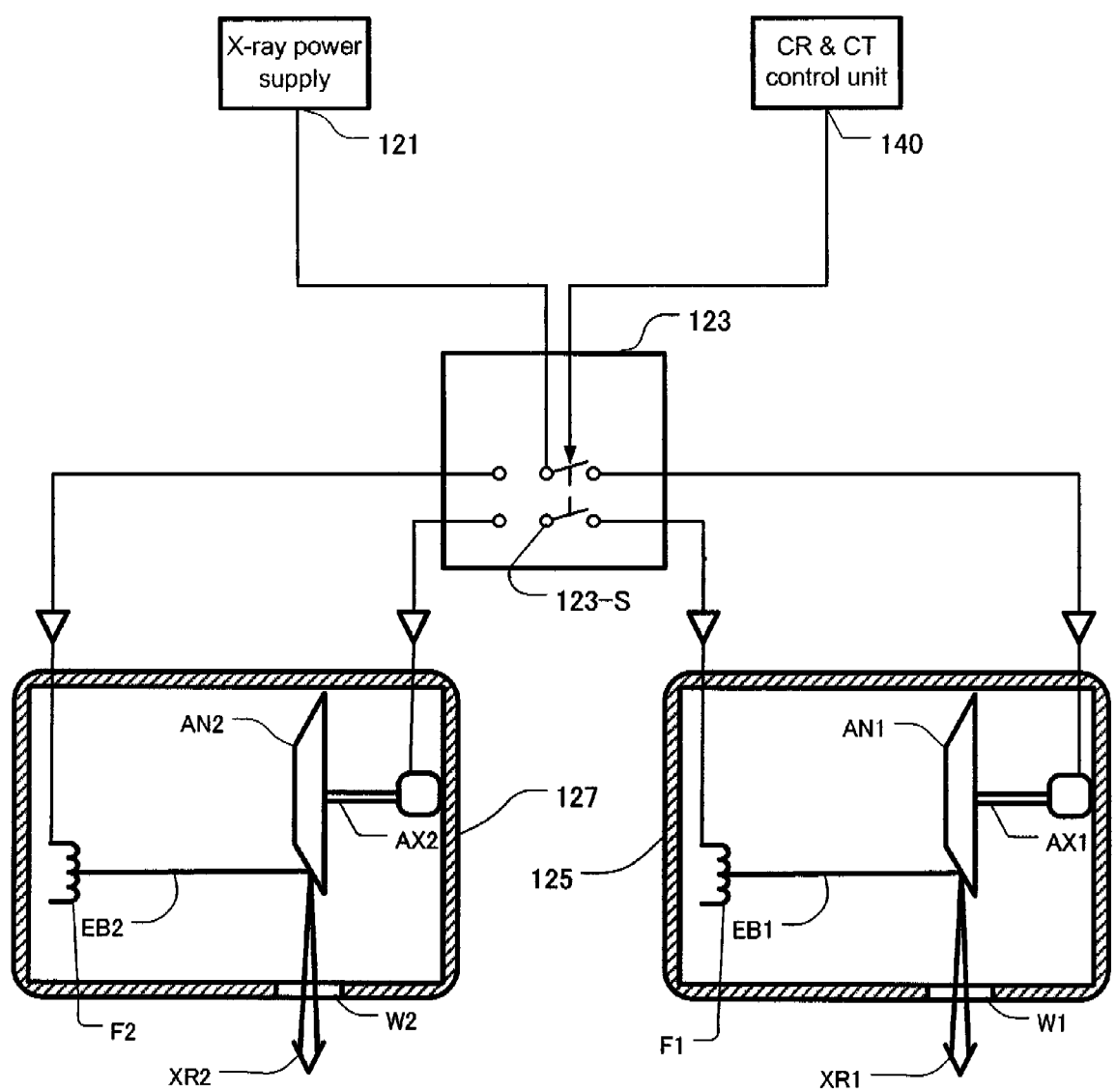
FIG. 14 is a block diagram representing control exercised by an X-ray tube controller 123 over X-ray tube 125 and X-ray tube 127.

As shown in FIG. 14, the X-ray tube controller 123 includes a switch 123-S, and the switch 123-S is under control of the CR & CT control unit 140. The switch 123-S is configured to selectively connect the X-ray power supply 121 either with a cathode filament F1 and a rotating anode motor AX1 of the X-ray tube 125 or with a cathode filament F2 and a rotating anode motor AX2 of the X-ray tube 127. The motors AX1 and AX2 are coupled with the rotating anodes AN1 and AN2, respectively.

As shown in FIG. 14, an electron beam EB1 generated from the anode filament F1 of the X-ray tube 125 and an electron beam EB2 generated from the anode filament F2 of the X-ray tube 127 are emitted to surfaces of the rotating anodes AN1 and AN2, respectively. When electrons strike the rotating anode AN1 and AN2, X-ray beams XR1 and XR2 generate from X-ray focal points. The X-ray beams XR1 and XR2 are emitted through the transparent windows W1 and W2, respectively, toward the subject.

Figure 15:
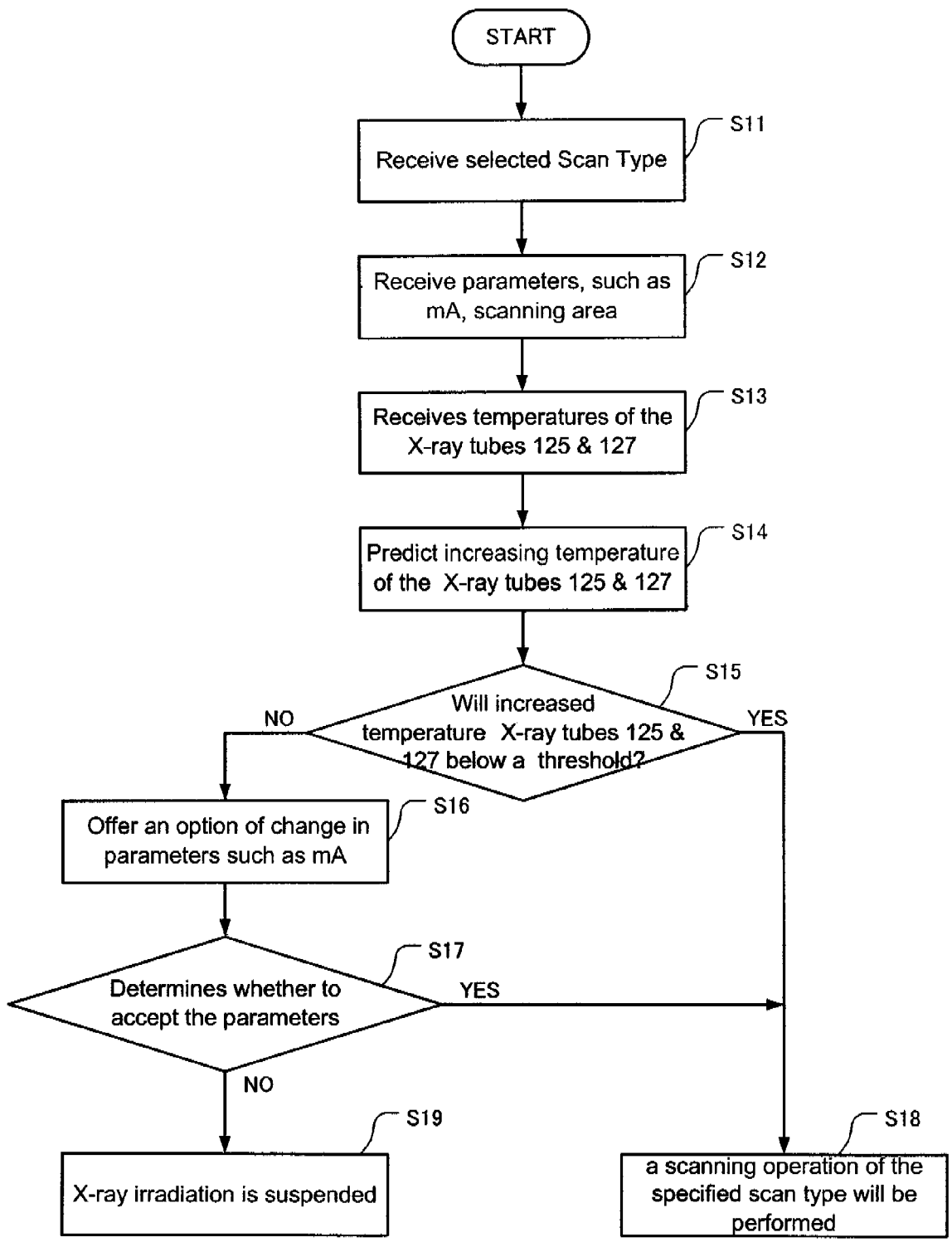
FIG. 15 is a flowchart showing a measure to prevent overheating of each X-ray tube.

The X-ray irradiation control will be describe in detail with reference to the flowchart shown in FIG. 15. In describing the control, particularly, the measures to prevent overheating of each X-ray tube will be brought up for discussion.

In step S11, a scan type input or specified by an operator using the keyboard 57 and/or the mouse 58 is received by the control console 50. The input scan type may for example be selected from four types as shown in FIG. 13.

Next, in step S12, if the input scan type indicates that the selected operation involves a CT scan operation, the control console 50 retrieves parameters related to the X-ray tube, such as a current (mA), a pre series delay (PSD) and an interval group delay (IGD), as well as a scanning area. The PSD is a parameter indicative of scanning timing of the CT scan, and the IDG is a parameter indicative of an interval of pulses in the current (mA) changing according to the rotation speed of the rotor 130.

In step S13, the control console 50 receives information on an instantaneous temperature of the X-ray tube 125 for the CT unit 101 or the X-ray tube 127 for the CR unit 103 from a temperature sensor which is not shown but provided in each X-ray tube 125, 127. In step S14, the control console 50 predicts increase in temperature of the first or second X-ray tube 125, 127 which will be caused by the following X-ray irradiation, based upon information such as the scan type received in step S111, or the parameters retrieved in step S12.

In step S15, the control console 50 determines whether the predicted increase in the temperature of the first or second X-ray tube 125, 127 shows that the increased temperature will remain on or below a predetermined threshold. If it is determined that the increased temperature will remain on or below the threshold, then the process goes to step S18, where a scanning operation of the specified scan type will be performed in a manner consistent with specs input by the operator. If it is determined that the increased temperature would exceed the threshold, then the process goes to step S16.

In step S16, alternative parameters are displayed on the monitor 56 of the operation console 50 to offer an option of change in irradiation conditions of the X-ray tubes 125 and 127 (e.g., parameters such as electric current (mA) for holding the temperature on or below the threshold). In step S17, the operator determines whether to accept the parameters displayed on the monitor 56. If the operator determines to accept the parameters, the operator changes the parameters as offered. Then, the process goes to step S18, where a scanning operation of the specified scan type will be performed with the parameters changed. If the operator determines not to change the parameters, then the process goes to step S19 where the X-ray irradiation is suspended.

If the above-described measures to prevent overheating of each X-ray tube are taken, frequency of replacing the X-ray tubes can be reduced, and the possibility of breakdown of the X-ray tubes can be reduced, with the result that the maintenance cost can be lowered.

INDUSTRIAL APPLICABILITY

In the illustrated embodiments, medical X-ray hybrid diagnosis systems 100 with a CR unit and a CT unit combined together and incorporated therein have been described by way of example. However, the X-ray hybrid diagnosis system consistent with the present invention may be combined with any other systems; for example, X-ray CT-PET systems, and X-ray CT-SPECT systems may be embodied according to the present invention. Further, in the above-exemplified embodiments, the CR unit is described as a digital X-ray radiography system, but any analog X-ray radiography systems using a film may be adopted. In this instance, a scanner for converting the film into digital images may be provided.

It is contemplated that numerous modifications may be made to the exemplary embodiments of the invention without departing from the spirit and scope of the embodiments of the present invention as defined in the following claims.

What is claimed is:

1. An X-ray hybrid diagnosis system comprising:
   an X-ray radiography unit comprising a first X-ray tube and a first X-ray detector for detecting X-rays irradiated from said first X-ray tube, said X-ray radiography unit configured to irradiate a subject with X-rays from said first X-ray tube to obtain an X-ray radiographic image;
   an X-ray CT unit comprising a gantry including a second X-ray tube and a second X-ray detector for detecting X-rays irradiated from said second X-ray tube, said X-ray CT unit configured to irradiate the subject with X-rays from said second X-ray tube and acquire projection data from a beam of X-rays that has passed through the subject to reconstruct an image using the acquired projection data and to obtain a tomographic image;
   a power supply configured to power said first X-ray tube and said second X-ray tube;
   a control console configured to control one of said X-ray radiography unit and said X-ray CT unit, said control console including a means for predicting an increase in temperature of one of said first X-ray tube and said second X-ray tube to control irradiation to maintain the temperature at or below a predetermined threshold; and
   a cradle, said first X-ray detector movably positioned within said cradle.

2. The X-ray hybrid diagnosis system according to claim 1 wherein said cradle is commonly usable for the subject to be irradiated with X-rays from one of said first X-ray tube said second X-ray tube.

3. The X-ray hybrid diagnosis system according to claim 2, wherein said first X-ray detector is located inside said cradle.

4. The X-ray hybrid diagnosis system according to claim 2, wherein said cradle is bendable in structure.

5. The X-ray hybrid diagnosis system according to claim 1, wherein said control console further comprises:
   a first mode in which the X-ray radiographic image is obtained by said X-ray radiography unit, and thereafter the projection data is acquired using said X-ray CT unit; and
   a second mode in which the projection data is acquired using said X-ray CT unit, and thereafter the X-ray radiographic image is obtained by said X-ray radiography unit.

6. The X-ray hybrid diagnosis system according to claim 1, wherein said control console further comprises:

a first mode in which the X-ray radiographic image is obtained by said X-ray radiography unit, and thereafter the projection data is acquired using said X-ray CT unit;

a second mode in which the projection data is acquired using said X-ray CT unit, and thereafter the X-ray radiographic image is obtained by said X-ray radiography unit;

a third mode in which the X-ray radiographic image is obtained by said X-ray radiography unit;

a fourth mode in which the projection data is acquired using said X-ray CT unit.

7. The X-ray hybrid diagnosis system according to claim 1, wherein said control console comprises means for offering an option of change in irradiation conditions of one of said first X-ray tube and said second X-ray tube, if said control console predicts an increase in the temperature beyond a predetermined threshold.

8. An X-ray hybrid diagnosis system comprising:

an X-ray radiography unit comprising a first X-ray tube and a first X-ray detector for detecting X-rays irradiated from said first X-ray tube, said X-ray radiography unit is configured to irradiate a subject with X-rays from said first X-ray tube to obtain an X-ray radiographic image;

an X-ray CT unit comprising a gantry including a second X-ray tube and a second X-ray detector for detecting X-rays irradiated from said second X-ray tube, said X-ray CT unit configured to irradiate the subject with X-rays from said second X-ray tube and acquire projection data from a beam of X-rays that has passed through the subject to reconstruct an image using the acquired projection data and to obtain a tomographic image;

a power supply configured to power said first X-ray tube and said second X-ray tube;

a control console configured to control said X-ray radiography unit and said X-ray CT unit; and a cradle that is commonly usable for the subject to be irradiated with X-rays from one of said first X-ray tube and said second X-ray tube, said cradle movable into and out from said gantry, and said first X-ray detector movably positioned within said cradle.

9. The X-ray hybrid diagnosis system claim 8, wherein said control console comprises a means for predicting an increase in temperature of one of said first X-ray tube and said second X-ray tube to control irradiation to maintain the temperature at or below a predetermined threshold.

10. The X-ray hybrid diagnosis system according to claim 8, wherein said control console comprises means for offering an option of change in irradiation conditions of one of said first X-ray tube and said second X-ray tube, if said control console predicts an increase in the temperature beyond a predetermined threshold.

11. The X-ray hybrid diagnosis system according to claim 8 further comprising a driving unit that raises said cradle to an upright position to facilitate X-ray radiography unit obtaining an X-radiographic image.

12. The X-ray hybrid diagnosis system according to claim 11, wherein said driving unit comprises one of an air cylinder and an electric motor to raise said cradle.

13. The X-ray hybrid diagnosis system according to claim 8, wherein said cradle comprises a guide rail to facilitate moving said first X-ray detector to a specific location within said cradle.

14. The X-ray hybrid diagnosis system according to claim 8, wherein said cradle comprises a transparent window that facilitates viewing said first-X-ray detector located inside said cradle.

15. An X-ray hybrid diagnosis system comprising:

an X-ray radiography unit comprising a frame, a first X-ray tube situated at said frame such that said first X-ray tube is able to rotate, and a first X-ray detector situated at said frame such that said first X-ray detector is able to one of move vertically and rotate, said first X-ray detector configured to detect X-rays irradiated from said first X-ray tube, and said X-ray radiography unit configured to irradiate a subject with X-rays from said first X-ray tube to obtain an X-ray radiographic image;

an X-ray CT unit comprising a gantry including a second X-ray tube and a second X-ray detector configured to detect X-rays irradiated from said second X-ray tube, said X-ray CT unit configured to irradiate the subject with X-rays from said second X-ray tube and acquire projection data from a beam of X-rays that has passed through the subject to reconstruct an image using the acquired projection data and to obtain a tomographic image;

a power supply configured to power said first X-ray tube and said second X-ray tube;

a control console configured to control said X-ray radiography unit and said X-ray CT unit; and a cradle assembly that is commonly usable for the subject to be irradiated with X-rays from one of said first X-ray tube and said second X-ray tube, said cradle assembly comprising a first cradle movable into and out from said gantry and a second cradle tiltable relative to said first cradle and coupled to said first cradle, said second cradle serving as an auxiliary to said first cradle.

16. The X-ray hybrid diagnosis system claim 15, wherein said control console comprises a means for predicting an increase in temperature of one of said first X-ray tube and said second X-ray tube to control irradiation to maintain the temperature at or below a predetermined threshold.

17. The X-ray hybrid diagnosis system according to claim 15, wherein said control console comprises means for offering an option of change in irradiation conditions of one of said first X-ray tube and said second X-ray tube, if said control console predicts an increase in the temperature beyond a predetermined threshold.

18. The X-ray hybrid diagnosis system according to claim 15, wherein said cradle assembly further comprises a driving unit that is able to one of horizontally move and tilt said second cradle.

19. The X-ray hybrid diagnosis system according to claim 15, wherein said control console comprises:

a first mode in which the X-ray radiographic image is obtained by said X-ray radiography unit, and thereafter the projection data is acquired using said X-ray CT unit; and a second mode in which the projection data is acquired using said X-ray CT unit, and thereafter the X-ray radiographic image is obtained by said X-ray radiography unit.

* * * * *